United States Patent
Roney et al.

(10) Patent No.: US 7,654,143 B2
(45) Date of Patent: Feb. 2, 2010

(54) METHOD AND APPARATUS FOR IN-SITU INSPECTION OF ROTARY MACHINE COMPONENTS

(75) Inventors: Robert M. Roney, Schoharie, NY (US); Richard M. Hatley, Convent Station, NJ (US)

(73) Assignee: General Electric Company, Schenectady, NY (US)

( * ) Notice: Subject to any disclaimer, the term of this patent is extended or adjusted under 35 U.S.C. 154(b) by 339 days.

(21) Appl. No.: 11/732,439

(22) Filed: Apr. 3, 2007

(65) Prior Publication Data

US 2008/0245151 A1    Oct. 9, 2008

(51) Int. Cl.
    *G01N 29/04*    (2006.01)
(52) U.S. Cl. ........................................................ 73/620
(58) Field of Classification Search .................. None
    See application file for complete search history.

(56) References Cited

U.S. PATENT DOCUMENTS

| | | | |
|---|---|---|---|
| 4,468,620 A | | 8/1984 | Vaerman ..................... 324/261 |
| 4,502,331 A | * | 3/1985 | Singh et al. ................... 73/627 |
| 4,843,884 A | * | 7/1989 | House et al. .................. 73/622 |
| 5,670,879 A | * | 9/1997 | Zombo et al. ............... 324/227 |
| 6,532,840 B2 | | 3/2003 | Hatley et al. ............... 73/866.5 |
| 6,707,297 B2 | | 3/2004 | Nath et al. ................... 324/240 |
| 6,725,722 B1 | | 4/2004 | Murphy et al. ................ 73/628 |
| 6,854,332 B2 | * | 2/2005 | Alleyne ....................... 73/636 |
| 7,174,788 B2 | | 2/2007 | Czerw et al. |
| 7,302,851 B2 | | 12/2007 | Czerw et al. |
| 2005/0126291 A1 | * | 6/2005 | Czerw et al. .................. 73/589 |
| 2006/0236769 A1 | * | 10/2006 | Tenley et al. .................. 73/618 |
| 2008/0250860 A1 | * | 10/2008 | Clossen-von Lanken Schulz et al. .......................... 73/627 |

FOREIGN PATENT DOCUMENTS

JP           10282070 A   * 10/1998
WO    WO 2005119242 A1   * 12/2005

* cited by examiner

*Primary Examiner*—Hezron Williams
*Assistant Examiner*—Rose M Miller
(74) *Attorney, Agent, or Firm*—James W. Pemrick; Ernest G. Cusick; Frank A. Landgraff (57) ABSTRACT

A method and apparatus for the inspection of rotary machine components is provided. A positioning fixture is clamped to the component to be inspected, and supports a transceiver that is used during the inspection. The positioning fixture can be navigated through and between rotary machine components to the desired location to be inspected. In one example, an ultrasonic transceiver can be used to perform the inspection. The apparatus can be used to perform in-situ inspections.

17 Claims, 7 Drawing Sheets

METHOD AND APPARATUS FOR IN-SITU INSPECTION OF ROTARY MACHINE COMPONENTS

BACKGROUND OF THE INVENTION

The present invention relates generally to in-situ inspection of rotating machinery components and, more particularly to in-situ ultrasonic inspection of turbine and compressor components, for example, blades, buckets or airfoils in turbines and compressors.

At least some known gas turbine engines include a compressor for compressing air, which is mixed with a fuel and channeled to a combustor wherein the mixture is ignited within a combustion chamber for generating hot combustion gases. The hot combustion gases are channeled downstream to a turbine, which extracts energy from the combustion gases for powering the compressor, as well as producing useful work to propel an aircraft in flight or to power a load, such as an electrical generator.

Known compressors include a rotor assembly that includes at least one row of circumferentially spaced rotor blades. Each rotor blade includes an airfoil that includes a pressure side and a suction side connected together at leading and trailing edges. Each airfoil extends radially outward from a rotor blade platform. Each rotor blade also includes an attachment portion, such as, a dovetail that extends radially inward from the platform, and is used to mount the rotor blade within the rotor assembly to a rotor disk or spool.

During operation, the rotor blades and dovetails are subjected to loading forces that may cause in-service cracking, micro-fractures or other damage that is visually imperceptible. Known inspection techniques are limited in their ability to assess the integrity of the blades while the blades are in-place. More specifically, a visual inspection only permits a limited examination of the blades for cracks in the airfoil. To thoroughly examine the blade and dovetail regions, where cracking or other damage may originate, at least a portion of the engine casing may need to be removed to facilitate removal of each blade, and subsequent inspection of the blades and dovetails with visual, magnetic particle, liquid penetrant, or other techniques. However, because of labor and cost constraints such techniques may be impracticable in some instances. To examine the blades without disassembly, a technician must manually reach into the machine. This can be a potentially hazardous action as any movement in the rotor blades or inlet guide vanes would likely result in the loss of a limb. Accordingly, a new method and apparatus for the in-situ inspection of rotating machinery components is needed.

BRIEF DESCRIPTION OF THE INVENTION

In one aspect, a method of testing a component of a rotary machine while the component remains coupled within an assembled rotary machine is provided. The method includes positioning a transceiver on a face of the component, transmitting ultrasonic waves into the component, receiving ultrasonic echoes, and analyzing the ultrasonic echoes.

In another aspect, an ultrasonic testing system for testing a component of a rotatable member of a rotary machine while the rotatable member remains coupled within an assembled rotary machine is provided. The system includes an ultrasonic transceiver configured to transmit ultrasound waves into and receive ultrasound echoes from the component, a processor for controlling outputs from the transmitter/receiver and receiving inputs from the transmitter/receiver, and a display for outputting information based on the ultrasonic echo data.

In another aspect, an in-situ ultrasonic testing apparatus for testing a component of a rotatable member of a rotary machine while the rotatable member remains coupled within an assembled rotary machine is provided. A positioning fixture includes clamping means for clamping onto the component, transceiver support means for mounting an ultrasonic transceiver, and manipulator rod means for enabling the transceiver to be moved to different positions along said component.

DETAILED DESCRIPTION OF THE INVENTION

Figure 1:
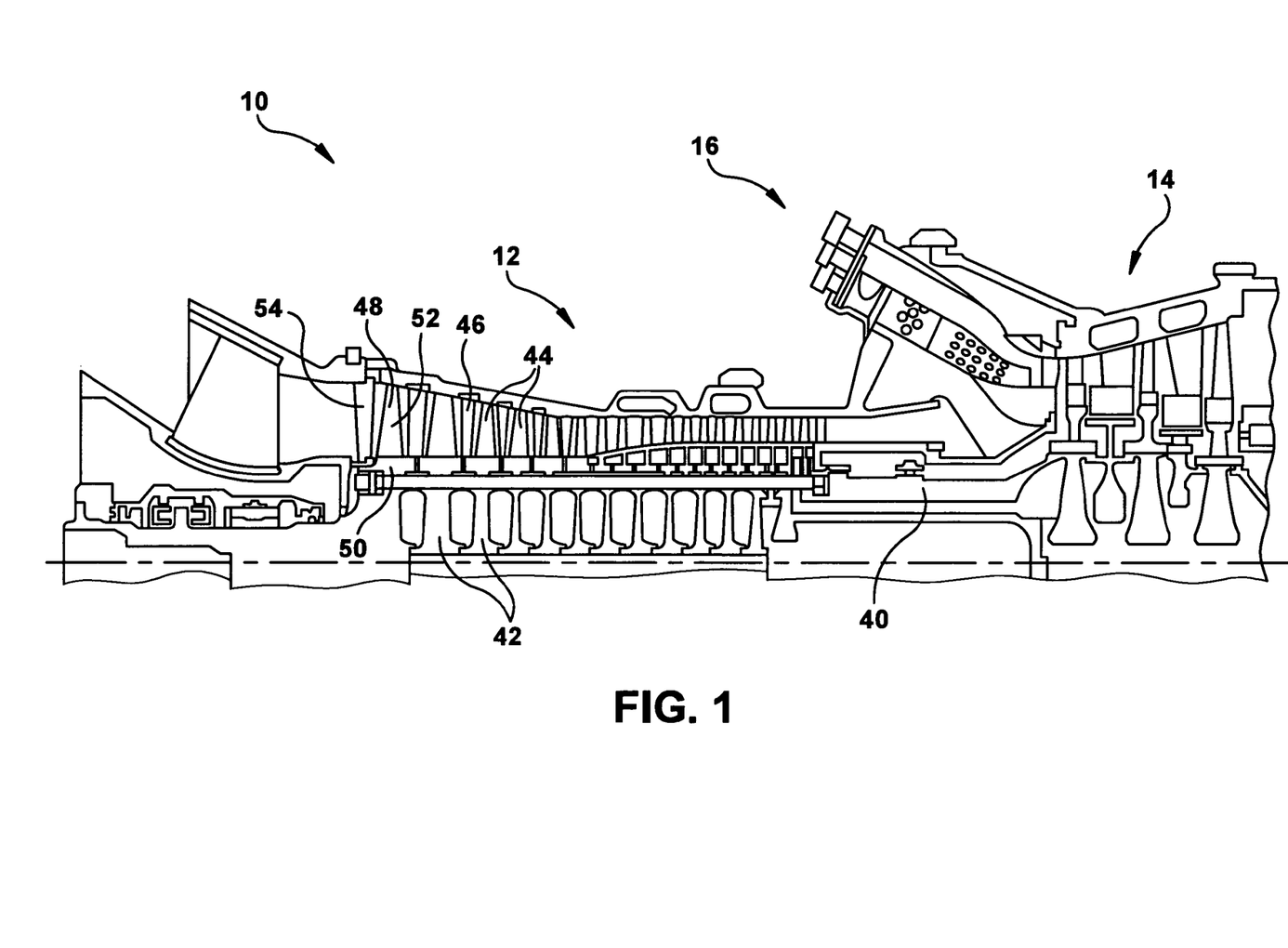
FIG. 1 is a side elevation view of an exemplary gas turbine engine.
Figure 2:
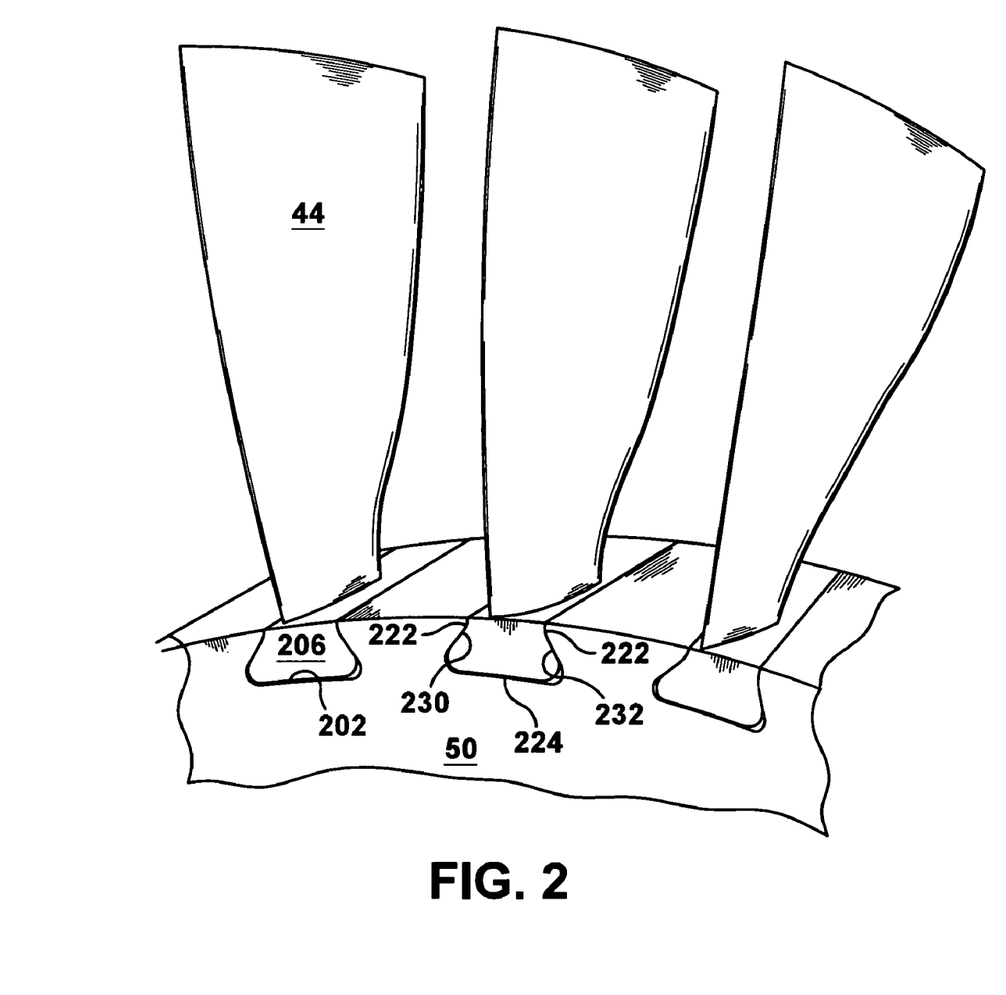
FIG. 2 is a perspective view of a portion of a row one (R1) compressor wheel that may be used with the gas turbine engine shown in FIG. 1.

FIG. 1 is a side elevation view of an exemplary gas turbine engine 10 that includes a compressor section 12, a turbine section 14 and a plurality of combustors 16 (only one combustor is shown in FIG. 1). Engine 10 includes a rotor 40 including a plurality of rotor wheels 42. Each rotor wheel 42 is configured to mount a plurality of components, such as, but not limited to, buckets or blades 44, which in conjunction with a respective number of stator vanes 46, form the various stages of engine 10. Hereafter, the description of the invention references the component as a blade, however, this description is merely exemplary. It is not intended to limit the invention in any manner. The invention herein contemplates use with any such component. In the exemplary embodiment, a plurality of compressor blades 44 are coupled to a first row 48 that includes a first-stage rotor wheel 50. Each blade 44 includes an airfoil 52 that is mounted in opposition to respective stator vanes 46. Blades 44 are spaced circumferentially about first-stage wheel 50. Inlet guide vanes 54 serve to properly orient the incoming airflow. The inlet guide vanes can be of the fixed or variable type. The variable type can open or close by varying amounts to adjust the angle of the incoming airflow. Turbine engine 10 may drive a generator (not shown) for producing electrical power FIG. 2 is a perspective view of a portion of first stage rotor wheel 50. Rotor wheel 50 includes a plurality of axially aligned dovetail slots 202 that are spaced circumferentially about a radially outer periphery of wheel 50. Slots 202 receive an attachment portion, such as a dovetail 206 of blade 44, therein. More specifically, blades 44 are removably coupled within disk slot 202 by each respective blade dovetail 206. Accordingly, slot 202 is shaped to generally compliment a shape of each dovetail 206 received therein, and accordingly, in the exemplary embodiment, includes a pair of wheel post tangs 222 and a disk slot bottom 224 that extends between wheel post tangs 222. In the exemplary embodiment, disk slot 202 also includes a pair of opposed wheel faces 230 and 232.

Figure 3:
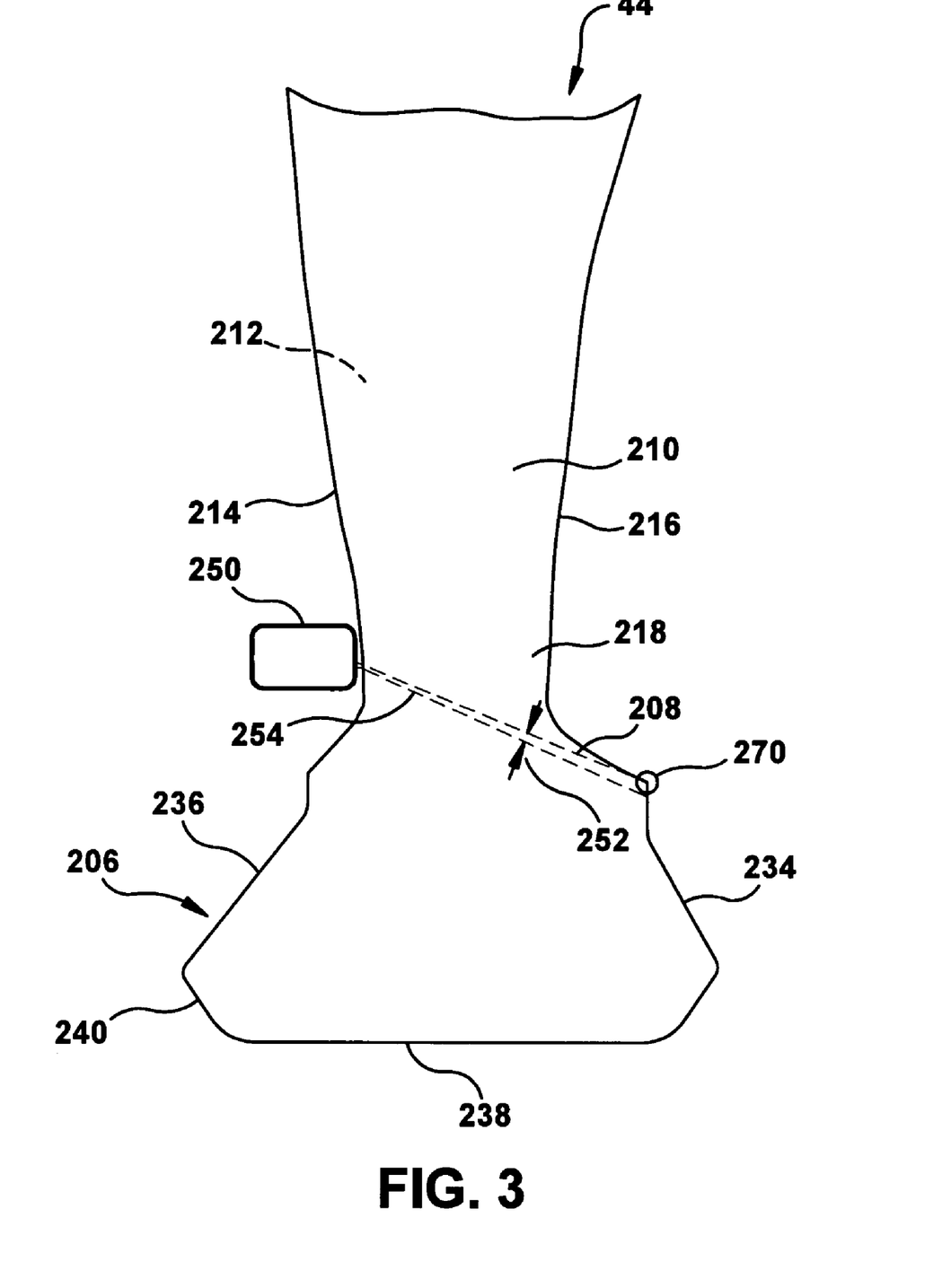
FIG. 3 is an enlarged axial cross-sectional view of a portion of a compressor blade that may be used with the compressor wheel shown in FIG. 2.

FIG. 3 is an enlarged axial cross-sectional view of a portion of rotor blade 44. Each rotor blade 44 includes a dovetail 206 used for mounting each respective airfoil 52 to rotor wheel 50. More specifically, each airfoil 52 extends radially outward from a platform 208 formed integrally with, and extending between dovetail 206 and airfoil 52. Each airfoil 52 includes a first contoured sidewall 210 and a second contoured sidewall 212. First sidewall 210 defines a suction side of airfoil 52, and second sidewall 212 defines a pressure side of airfoil 52. Sidewalls 210 and 212 are joined at a leading edge 214 and at an axially spaced trailing edge 216 of airfoil 52. More specifically, airfoil trailing edge 216 is spaced downstream from airfoil leading edge 214. First and second sidewalls 210 and 212, respectively, extend longitudinally or radially outward in span from a blade root 218 positioned adjacent dovetail 206, to an airfoil tip 220.

Each blade dovetail 206 is mounted within dovetail slot 202 (refer to FIG. 2), and cooperates with dovetail slot 202, to form rotor wheel 50. In the exemplary embodiment, each dovetail 206 includes a pair of opposed dovetail shoulders 234 and 236, and a dovetail bottom 238 that extends between dovetail shoulders 234 and 236. A dovetail base 240 extends circumferentially between dovetail shoulders 234 and 236. Shoulders 234 and 236 are sized to be received within respective wheel post tangs 222 and engage disk slot 202, such that blades 44 are radially retained within wheel 50. In an alternative embodiment, each blade dovetail includes a plurality of pairs of wheel post tangs 222.

During operation, centrifugal forces force rotor blades 44 outward and induce loading forces into dovetail 206 and blade 44. Over time, such forces may induce cracking within dovetail 206 at such locations that may be radially inward or outward from platform 208, and thus not easily accessible to conventional testing techniques. As one example, an area where cracks may develop is indicated by the circle 270.

An ultrasonic transceiver 250 may be placed in a position contacting blade 44 radially outward from platform 208 to interrogate, inspect and scan, as described hereinafter a volume of dovetail 206 that is inaccessible to known testing techniques. Inaccessible is defined as a location that cannot be reached without disassembling parts of the machine, or that poses a hazardous condition to a testing technician. For example, to access the R0 blades (i.e., the first row of blades) in a compressor, a technician must reach through the inlet guide vanes (IGVs) 54 with his hand and arm. This is extremely dangerous for the technician as any movement of the IGVs or the R0 blades could result in the loss of a hand and/or an arm. Accordingly, the present invention provides an improved safer method and apparatus for inspecting rotary machine components.

In the exemplary embodiment, transceiver 250 is a monolithic type ultrasonic transceiver wherein an angle and focus of a single ultrasonic beam 254 are selected by controlling the physical orientation of transceiver 250. The beam spread 252 is selected to cover the desired area to be inspected, such as, that indicated by region 270. During scanning, or the inspection process, an ultrasonic beam 254 from transceiver 250 penetrates into blade 44 and dovetail 206. As each blade 44 is scanned, the ultrasonic transceiver 250 generates ultrasonic pulses, and then receives echoes from blade 44 to facilitate detecting flaws, which may have developed within blade 44 or dovetail 206. The data received is indicative of the structure and/or a flaw in blade 44 or dovetail 206. This process of steps can be referred to as interrogating, inspecting or scanning. In alternative embodiments, transducer 250 comprises at least one non-phased array transducer configured to transmit ultrasonic beams into a component at a plurality of steering angles or at least one linear phased array type. Using one or more transducers may permit ultrasonic viewing of portions of the component that may not be able to be viewed using traditional techniques.

A monolithic transceiver is a device that generates only one ultrasonic beam at a time, however, there may be one or more ultrasonic generating elements in this type of transceiver. A phased array ultrasonic transceiver generates one or more ultrasonic beams simultaneously (or in rapid sequence) at multiple angles. This allows dynamic focusing and "electronic" steering of the beam and multiple beam widths. Another advantage of phased array type transceivers is their wide field of view. Components may be tested separately from other pieces of an assembly as well as part of the assembly. In addition, components with portions that are inaccessible to known testing methods may be tested using one or more monolithic transceivers, one or more non-phased-array transceivers and/or one or more phased-array transducers.

Figure 4:
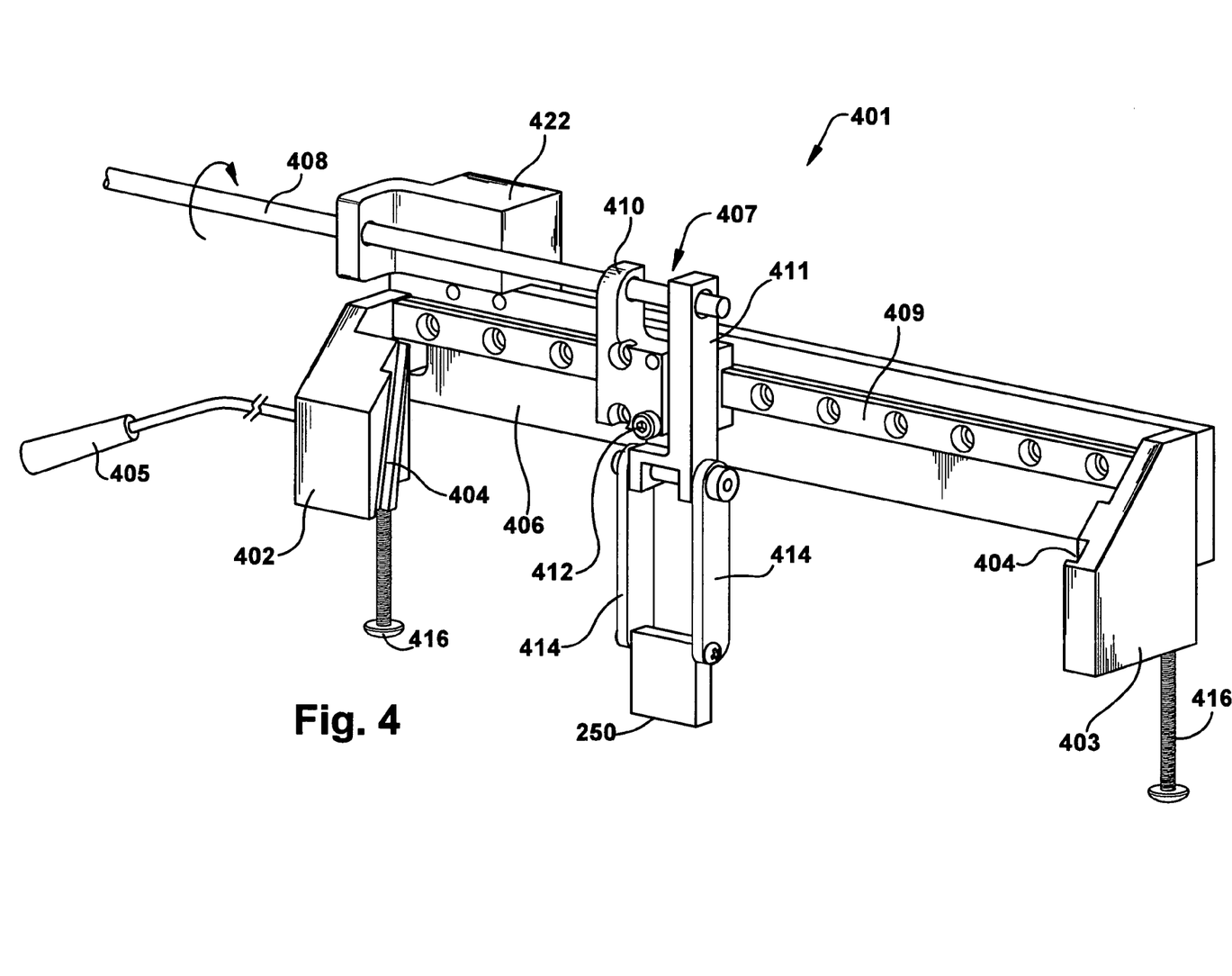
FIG. 4 is a perspective view of the clamp and manipulating means.

FIG. 4 is an enlarged perspective view of an exemplary clamp and manipulating means 401, as embodied by the invention. The clamps 402, 403 attach to the leading and trailing edges of the blade 44. The clamps comprise elongated slots 404 which engage the edges of blades 44 to securely mount the clamp and manipulating means 401 to the blade 44. Handle 405 is used to maneuver and navigate the clamp and manipulating means 401 inside the rotary machine and onto a blade 44. Clamp 402 is hingedly connected to base 406. This hinge or pivot 602 (not illustrated in FIG. 4, but shown in FIG. 6) allows the clamps 402 and 404 to open to accept the blade, then close to engage and securely mount to the blade 44. The handle 405 is used to pivot clamp 402 between open and closed positions. Additionally, clamp 402 functions as a docking member for transceiver mount 407. As the clamp and manipulating means 401 is inserted inside the rotary machine, clamp 402 secures transceiver mount 407 and prevents any unwanted movement.

Manipulator rod 408 is used to move transceiver mount 407 back and forth along a rail 409 on the base 406. During the inspection procedure, manipulator rod 408 is used to reposition the transceiver 250 along the face of the component to be tested. The manipulator rod 408 is threaded into base 410 and fastened to a pivot arm 411 with suitable fasteners. Manipulator rod 408 can be passed through a support means 422. By rotating manipulator rod 408, the pivot arm 411 is forced away from or pulled towards threaded base 410, by pivoting on pivot 412. This enables the skew angle of the scan to be adjusted to re-aim the scan on specific areas of interest. The skew angle is the angle the incident beam 254 makes with the surface of the blade 44 or dovetail 206. Typically, the skew angle is about 90°, but can be changed to scan other areas, or to obtain a "different view" of a specific area of interest. The manipulator rod 408 enables the skew angle to be adjusted between about −45° to +45°.

Spring biased mounting arms 414 retain ultrasonic transceiver 250 and maintain contact between the component under test and the transceiver 250. For example, the spring biasing means could be a wire spring wound around shaft 420, having one end contacting the mounting arm 414 and the other end contacting pivot arm 411. Other spring biasing means that accomplish the same effect are also contemplated and within the scope of the invention. Height guides 416 contact the surface of the dovetail 206 or wheel 50 and maintain the correct spacing between the dovetail and transceiver 250. This orients and aims the ultrasonic transceiver 250 at the desired area to be inspected (e.g., area 270, as shown in FIG. 3). Height guides 416 are adjustable and can be set to various vertical offsets. In one embodiment, height guides 416 can comprise threaded bolts, and the height is adjusted by turning the bolts clockwise or counter-clockwise. In alternative embodiments, height guides could be telescopically adjustable members or segmented members with sections that can be added or removed to adjust the height.

Figure 5:
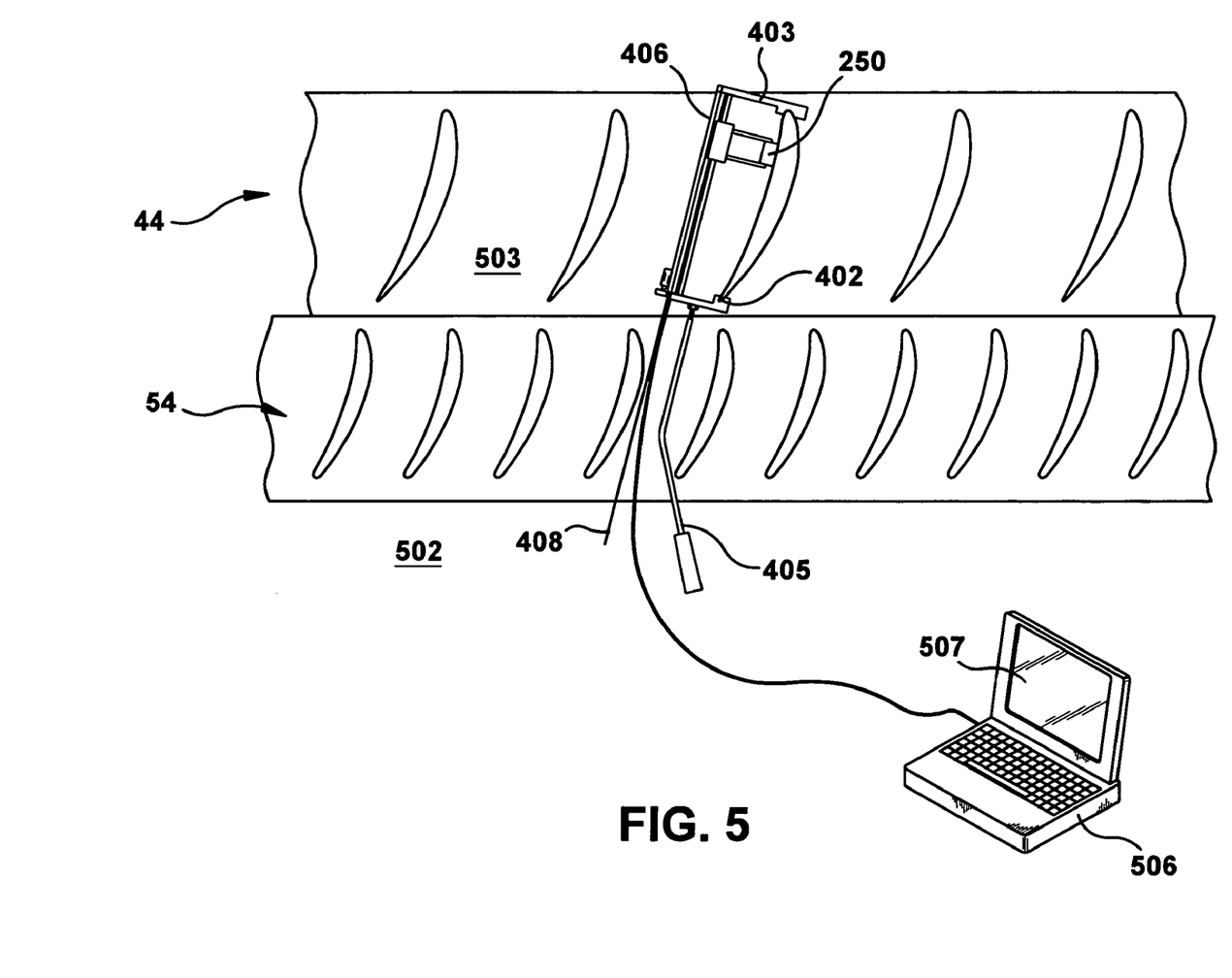
FIG. 5 is a radial perspective view of a row of inlet guide vanes and a row of compressor blades that may be used with the gas turbine engine shown in FIG. 1.

FIG. 5 is a radial perspective view of a row of inlet guide vanes 54 and a row of R0 compressor blades 44 in a gas turbine engine 10 (shown in FIG. 1). In one embodiment, transceiver 250 is transitioned from an accessible area 502 upstream from inlet guide vanes 54, through inlet guide vanes 54 to inaccessible area 503. In this exemplary embodiment, clamp and manipulating means 401, together with transceiver 250, are used in situ (i.e., the gas turbine engine 10 does not need to be dismantled). The inlet guide vanes 54 may be blocked in a full open position to facilitate testing of blades 44. Accessible area 502 is located outside of the compressor and inaccessible area 503 is located behind inlet guide vanes 54. Inaccessible area 503 was only previously accessible by dismantling the compressor and inlet guide vanes. This dismantling was a very time consuming and expensive process, as well as, costly due to the down time of the power generation equipment. Handle 405 and manipulator rod 408 can be extended to reach deeper rows of blades, such as, R1, R2, R3, etc. R0 typically refers to the first row of blades, and R1 to the second row and so on.

Transceiver 250 is held in place against each blade 44 in turn, and is translated mechanically, or by machine control, with manipulator rod 408, in a substantially axial direction across blade pressure side 212. During the scanning, an ultrasonic beam from transceiver 250 penetrates into blade 44 and dovetail 206. As each blade 44 is interrogated, the ultrasonic transceiver 250 generates ultrasonic pulses, and then receives echoes from blade 44 to facilitate detecting flaws, which may have developed within blade 44 or dovetail 206. The data received is indicative of the structure and/or a flaw in blade 44 or dovetail 206.

In the exemplary embodiment, the data is transmitted to a processor 506 such as, but not limited to a laptop computer, a personal digital assistant (PDA), a data collector, or a network connection. In an alternative embodiment, the echo data and transceiver position data may be received by separate processors. In the exemplary embodiment, processor 506 includes a display 507 to monitor and display the results of each scan and operation of the scan. As used herein, the term "processor" also refers to microprocessors, central processing units (CPU), application specific integrated circuits (ASIC), logic circuits, and any other circuit or processor capable of executing inspection system, as described herein.

Figure 6:
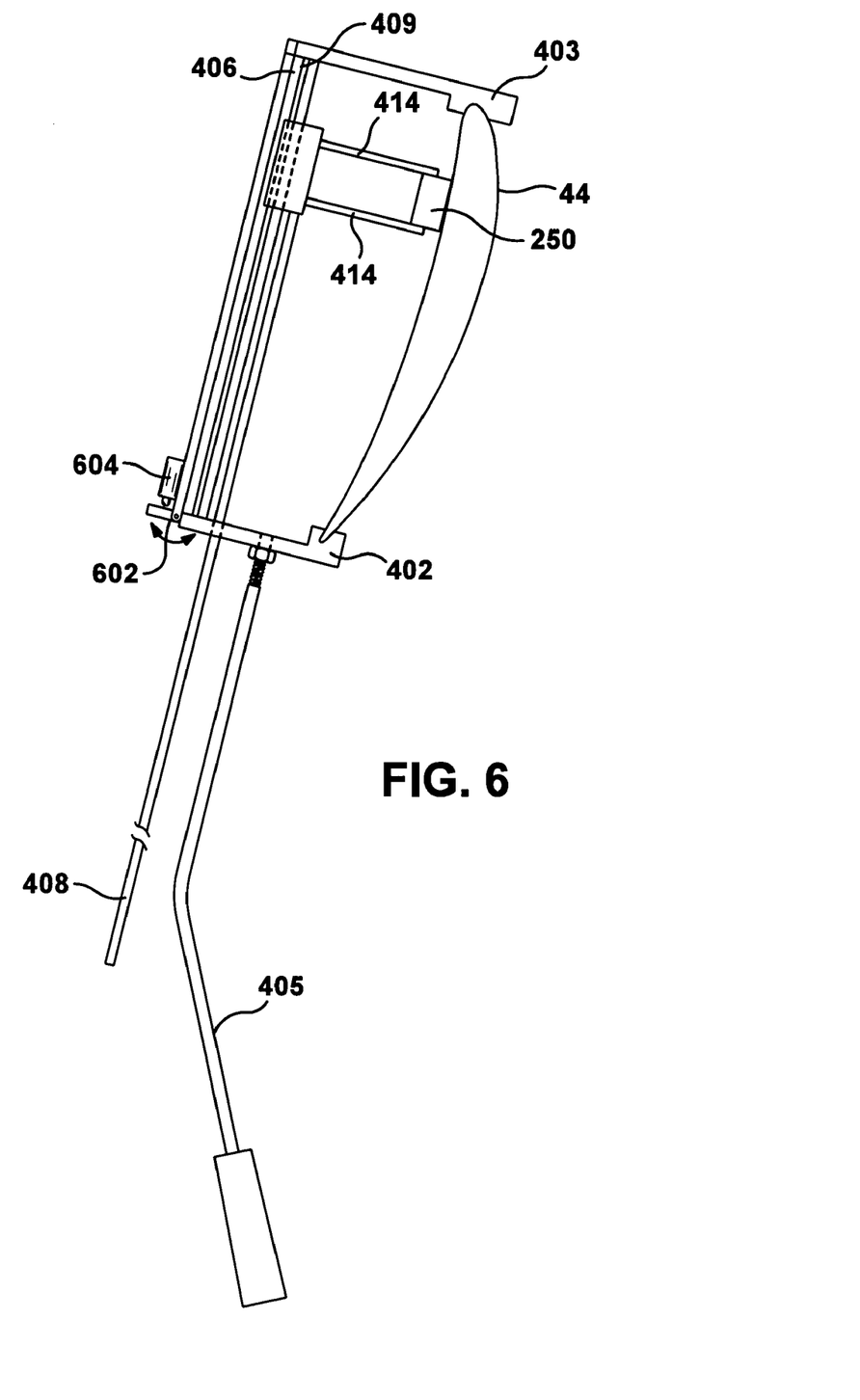
FIG. 6 is a cross-sectional view of the clamp and manipulating means attached to a compressor blade that may be used with the compressor wheel shown in FIG. 2.

FIG. 6 is a cross sectional view of clamp and manipulating means 401 attached to a blade 44. Pivot point 602 is located near one end of clamp 402. Biasing means 604 biases clamp 402 in a closed position. In one embodiment, biasing means 604 is comprised of a spring-loaded plunger mechanism. In an alternative embodiment, the biasing means 604 could be a pneumatic operating element, or any other feature that biases clamp 402 into its closed position (FIG. 6). An operator or technician can open clamp 402 by pulling on handle 405 pivoting 402 about pivot pin 602. This enables the clamps 402 and 403 to expand and accept the blade 403. When the handle 405 is released, clamp 402 closes and securely engages blade 44.

During operation, handle 405 and clamp and manipulating means 401 are extended through inlet guide vanes 54 from accessible area 502, where an operator may then attach the clamps 402 and 403 onto blade 44. The position of transceiver 250 with respect to blade 44 may be input by the user in response to prompts from processor 506. Processor 506 may include data acquisition and/or analysis software executing thereon that receives data from transceiver 250 that displays simultaneously the data recorded for all beam angles as a polar plot, creating a cross-sectional view called a "linear scan", "arc scan" or "sector scan" image. In the example of a linear scan, the ultrasonic transceiver is moved in a horizontal direction. For every scan line, a transmit pulse is sent and the reflected signals from different depths are recorded and scan-converted to be shown on a video display (e.g., 507). The single transducer movement during image acquisition determines the shape of the image. This movement directly translates into the shape of a linear array transducer, i.e., for the linear scan, the array would be straight, while for the arc scan, the array would be concave. The resulting scan image may include the echoes received from blade 44 or dovetail 206 and cracks or flaws located therein. The positions of the reflections may be measured directly from the resulting scan image. If a crack or flaw is present, its image will be displayed among the reflectors on display 507 or sent directly over a network to an analysis location (not shown). The position, depth, and dimension of the crack or flaw may be measured directly from the image shown on display 507.

The scan may be controlled manually by operator input to processor 506. Scan control software executing in processor 506 may control transceiver 250. At the end of the scan, processor 506 stops taking data and prompts the user to reposition clamp and manipulating means 401 to scan the next blade. Scanning continues with each blade scanned in turn until all blades and dovetails are scanned. Repositioning of rotor wheel 50 to maintain accessibility to blades 44 may be necessary.

Figure 7:
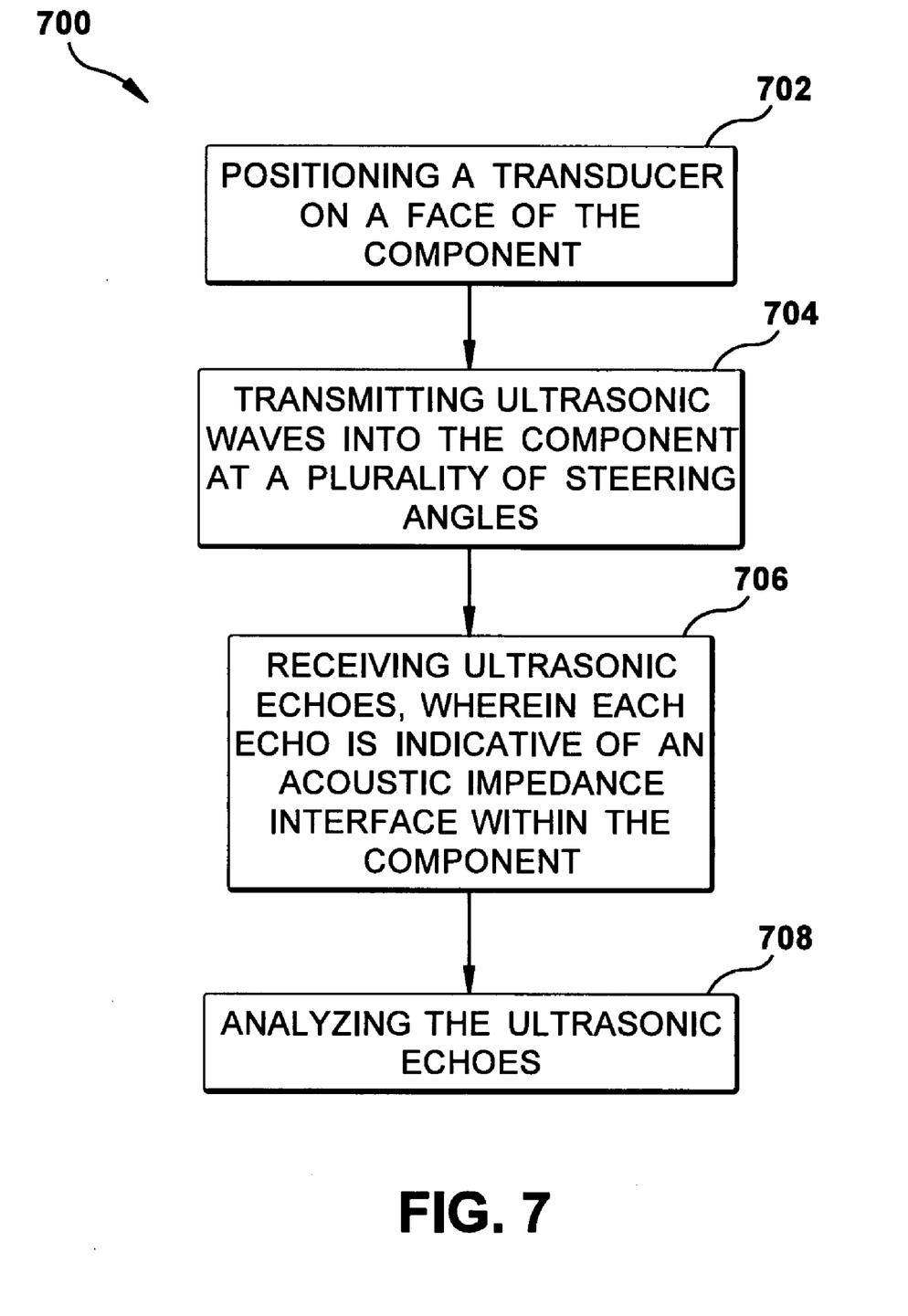
FIG. 7 is a block diagram of an exemplary method for ultrasonically testing a component of a rotating machine.

FIG. 7 is a block diagram of an exemplary method 700 for ultrasonically testing a component 44 of a rotatable member 50 of a rotary machine 10 while the rotatable member remains positioned within a casing (not shown) of an assembled rotary machine 10. In the exemplary embodiment, an ultrasonic transceiver is positioned at step 702, on a face of a turbine blade attached to a turbine rotor wheel. The transceiver is positioned on each blade in turn during the testing procedure. Because the turbine remains assembled during the testing, the transceiver is fed through the turbine inlet guide vanes 54, which may be blocked fully open. The transceiver is positioned at the base of the blade airfoil radially outward from the blade platform and slid axially along a predetermined scan path while in contact with the blade. During the scan, the transceiver transmits at step 704, ultrasonic waves into an inaccessible portion of the blade and dovetail such that the blade and dovetail may be interrogated by the ultrasonic waves. The transceiver receives at step 706, ultrasonic echoes as a result of the ultrasonic waves impinging on an acoustic impedance interface within the material and being reflected. The transceiver receives at least some of the ultrasonic energy that is reflected back into the transceivers' field of view. The echoes may be indicative of flaws, such as cracks, that may have developed within the blade and/or dovetail. The echoes are transmitted to a processor for analyzing at step 708, the ultrasonic echoes to determine the crack location and dimensions. The result may be displayed on a local display or may be transmitted to a remote location for further analysis.

The above-described ultrasonic testing method and apparatus is cost-effective and highly reliable for testing components that remain installed on a turbine rotor or compressor in an assembled machine. Specifically, the turbine or compressor blades are inaccessible to visual, eddy current, dye penetrant, and other test methods when the turbine is assembled. The method and apparatus permits an inspection of machine components without the heretofore attendant disassembly of the turbine and removal of the turbine or compressor blades to permit early detection of fatigue cracking in the primary location from which the cracks originate. The method and apparatus also enables a technician to perform an in-situ inspection without putting any part of their body in harm's way. By inspecting without removal of the component, the inspection is less disruptive to the commercial operation of the machines and can be easily scheduled and accomplished within scheduled downtimes. As a result, the methods and apparatus described herein facilitate ultrasonic testing in a cost-effective and reliable manner. The method and apparatus can be applied to the inspection of many types of rotating machines, such as, compressors, turbines, and generators, to name a few.

Exemplary embodiments of ultrasonic testing systems are described above in detail. The systems are not limited to the specific embodiments described herein, but rather, components of each system may be utilized independently and separately from other components described herein. Each system component can also be used in combination with other system components. For example, the ultrasonic transceiver could be replaced by an infrared, x-ray, electrical, resistive or other type of sensor.

While the invention has been described in terms of various specific embodiments, those skilled in the art will recognize that the invention can be practiced with modification within the spirit and scope of the following claims.

What is claimed is:

1. A method of inspecting a component of an assembly, said component coupled to a rotatable member of a rotary machine while the rotatable member remains coupled within an assembled rotary machine, said method comprising:
   providing a transceiver configured to transmit ultrasonic waves into and receive ultrasonic echoes from the component;
   providing a positioning fixture coupled to said transceiver and configured to position said transceiver across a face of the component, said positioning fixture including clamping means to clamp to said component, and wherein the positioning fixture includes a handle, said handle enabling the transceiver and positioning fixture to be navigated from an area outside of the rotary machine to an area inside the rotary machine;
   positioning said transceiver on a face of the component, wherein the step of positioning comprises attaching said clamping means to the component for securely mounting said transceiver on said component,
   transmitting ultrasonic waves into the component;
   receiving ultrasonic echoes; and
   analyzing the ultrasonic echoes.

2. A method in accordance with claim 1, wherein the step of transmitting ultrasonic waves comprises transmitting ultrasonic waves at a plurality of steering angles using a phased array transceiver.

3. A method in accordance with claim 1, wherein the step of transmitting ultrasonic waves comprises transmitting ultrasonic waves at a single angle using at least one monolithic transceiver.

4. A method in accordance with claim 1, wherein the component includes a portion that is inaccessible when the component is coupled to the assembly, said transmitting ultrasonic waves comprises directing the waves into an inaccessible portion of the component.

5. A method in accordance with claim 1, wherein said method further comprises a step of determining at least one of a flaw position and a flaw dimension from the echoes.

6. A method in accordance with claim 1, further comprising a step of repositioning the transceiver along the face of the component to conduct inspections of different areas of the component.

7. A method in accordance with claim 1, further comprising at least one of the steps of repositioning the transceiver and changing a skew angle of the transceiver using a manipulator rod.

8. An ultrasonic testing apparatus for testing a component of a rotary machine, said apparatus comprising:
   a transceiver configured to transmit ultrasound waves into and receive ultrasound echoes from the component;
   a positioning fixture coupled to said transceiver and configured to position said transceiver across a face of the component, said positioning fixture including clamping means to clamp to said component;
   wherein the positioning fixture includes a handle, said handle enabling the transceiver and positioning fixture to be navigated from an area outside of the rotary machine to an area inside the rotary machine.

9. An ultrasonic testing apparatus in accordance with claim 8, wherein the component comprises a component of a rotatable member of a rotary machine while the rotatable member remains coupled within an assembled rotary machine, and wherein said component is a compressor blade.

10. An ultrasonic testing apparatus in accordance with claim 8, wherein the component comprises a component of a rotatable member of a rotary machine while the rotatable member remains coupled within an assembled rotary machine, and wherein said component is a turbine blade.

11. An ultrasonic testing apparatus in accordance with claim 8, wherein the positioning fixture includes a manipulator rod, said manipulator rod enabling the transceiver to be moved along the face of the component and to change the skew angle of the transceiver.

12. An ultrasonic testing apparatus in accordance with claim 8, wherein said positioning fixture further comprises height guides, said height guides providing a predetermined offset from the base of the component to position said transceiver at a predetermined height relative to the base of the component.

13. An ultrasonic testing apparatus in accordance with claim 12, wherein said height guides are adjustable to provide multiple predetermined offsets from the base of the component to position said transceiver at multiple predetermined heights.

14. An ultrasonic testing apparatus in accordance with claim 8, wherein said clamping means comprises at least two clamps, and at least one clamp is pivotally or hindgedly connected to said positioning fixture.

15. An ultrasonic testing apparatus in accordance with claim 8, wherein said clamping means comprises at least two clamps, and at least one clamp is telescopically connected to said positioning fixture.

16. An ultrasonic testing apparatus in accordance with claim 8, wherein said positioning fixture further comprises transceiver mounting means, said mounting means for maintaining said transceiver in contact with said component.

17. An in-situ ultrasonic testing apparatus for testing a component of a rotatable member of a rotary machine while the rotatable member remains coupled within an assembled rotary machine, said apparatus comprising:

a positioning fixture comprising clamping means for clamping onto said component, transceiver support means for mounting an ultrasonic transceiver, manipulator rod means for enabling said transceiver to be moved to different positions along said component; and wherein said component is a blade, bucket or airfoil of a gas turbine, steam turbine, compressor or generator.

\* \* \* \* \*